US012564310B2

(12) United States Patent (10) Patent No.: US 12,564,310 B2
Yoshioka et al. (45) Date of Patent: Mar. 3, 2026

(54) ENDOSCOPE AND ENDOSCOPE APPARATUS

(71) Applicant: FUJIFILM Corporation, Tokyo (JP)

(72) Inventors: Masato Yoshioka, Kanagawa (JP);
Takeshi Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 929 days.

(21) Appl. No.: 17/484,891

(22) Filed: Sep. 24, 2021

(65) Prior Publication Data

US 2022/0007921 A1 Jan. 13, 2022

Related U.S. Application Data

(63) Continuation of application No. PCT/JP2020/006828, filed on Feb. 20, 2020.

(30) Foreign Application Priority Data

Mar. 29, 2019 (JP) ................................. 2019-068089

(51) Int. Cl.
*A61B 1/00* (2006.01)
*A61B 1/045* (2006.01)
(Continued)

(52) U.S. Cl.
CPC .... *A61B 1/00096* (2013.01); *A61B 1/000094* (2022.02); *A61B 1/00045* (2013.01);
(Continued)

(58) Field of Classification Search
CPC .... A61B 1/00096; A61B 1/0623–0625; G02B 23/243; G02B 23/2476; G02B 23/2461; G02B 5/04
See application file for complete search history.

(56) References Cited

U.S. PATENT DOCUMENTS 5,150,254 A * 9/1992 Saitou ...................... A61B 1/05
359/740
2014/0296638 A1 10/2014 Komukai
(Continued)

FOREIGN PATENT DOCUMENTS

CN 103987307 A 8/2014
JP 2002-095626 A 4/2002
(Continued)

OTHER PUBLICATIONS

International Search Report issued in PCT/JP2020/006828; mailed Apr. 21, 2020.
(Continued)

*Primary Examiner* — Alexandra L Newton
*Assistant Examiner* — Alexandra Newton Surgan
(74) *Attorney, Agent, or Firm* — Studebaker Brackett PLLC

(57) ABSTRACT

An auxiliary measurement light optical system of an endoscope is housed in a second hole portion. A transparent lid is provided at a distal end of the second hole portion and the second hole portion is closed by the transparent lid, so that the auxiliary measurement light optical system is housed behind the transparent lid. The transparent lid is formed in the shape of a plate, and one end surface of the transparent lid is formed of a flat surface. The transparent lid is disposed so that the flat surface is flush with the distal end of the second hole portion.

11 Claims, 14 Drawing Sheets

(51) Int. Cl.
  *A61B 1/06*    (2006.01)
  *A61B 5/06*    (2006.01)

(52) U.S. Cl.
  CPC .......... *A61B 1/00097* (2022.02); *A61B 1/045*
    (2013.01); *A61B 1/0676* (2013.01); *A61B*
               *5/064* (2013.01)

(56)        References Cited

U.S. PATENT DOCUMENTS

| | | | | |
|---|---|---|---|---|
| 2019/0086657 | A1* | 3/2019 | Sueyoshi | ............... A61B 1/051 |
| 2019/0204069 | A1* | 7/2019 | Tatsuta | ................... G02B 23/24 |
| 2019/0274591 | A1* | 9/2019 | Yokota | ................... H04N 23/56 |
| 2020/0107698 | A1 | 4/2020 | Tatsuta et al. | |

FOREIGN PATENT DOCUMENTS

| | | | |
|---|---|---|---|
| JP | 2013-009896 | A | 1/2013 |
| WO | 2013/094569 | A1 | 6/2013 |
| WO | 2018/051680 | A1 | 3/2018 |
| WO | 2019/017018 | A1 | 1/2019 |

OTHER PUBLICATIONS

International Preliminary Report On Patentability and Written Opinion issued in PCT/JP2020/006828; issued Sep. 28, 2021.

An Office Action mailed by China National Intellectual Property Administration on Oct. 28, 2023, which corresponds to Chinese Application No. 202080025717.5 and is related to U.S. Appl. No. 17/484,891; with English translation.

The extended European search report issued by the European Patent Office on Apr. 20, 2022, which corresponds to European Patent Application No. 20785071.0-1020 and is related to U.S. Appl. No. 17/484,891.

An Office Action; "Notice of Reasons for Refusal," mailed by the Japanese Patent Office on Aug. 2, 2022, which corresponds to Japanese Patent Application No. 2021-511214 and is related to U.S. Appl. No. 17/484,891; with English language translation.

An Office Action mailed by China National Intellectual Property Administration on Mar. 24, 2023, which corresponds to Chinese Patent Application No. 202080025717.5 and is related to U.S. Appl. No. 17/484,891; with English language translation.

Communication pursuant to Article 94(3) EPC issued by the European Patent Office on Jan. 24, 2024, which corresponds to European Patent Application No. 20785071.0-1020 and is related to U.S. Appl. No.17/484,891.

* cited by examiner

| CRUCIFORM SHAPE WITH GRADATIONS | DISTORTED CRUCIFORM SHAPE | CIRCULAR-AND-CRUCIFORM SHAPE | SHAPE OF MEASUREMENT POINT GROUP |
|---|---|---|---|

ENDOSCOPE AND ENDOSCOPE APPARATUS

CROSS-REFERENCE TO RELATED APPLICATIONS

This application is a Continuation of PCT International Application No. PCT/JP2020/006828 filed on 20 Feb. 2020, which claims priority under 35 U.S.C § 119(a) to Japanese Patent Application No. 2019-068089 filed on 29 Mar. 2019. The above application is hereby expressly incorporated by reference, in its entirety, into the present application.

BACKGROUND OF THE INVENTION

1. Field of the Invention

The present invention relates to an endoscope and an endoscope apparatus.

2. Description of the Related Art

In a case where an object to be observed is observed using an endoscope, a distance to the object to be observed is acquired. For example, in WO2018/051680A (corresponding to US2019/0204069A1), laser light of which an optical axis is inclined toward the optical axis of an image pickup optical system is emitted from an auxiliary measurement light optical system, which is provided away from the image pickup optical system, as auxiliary measurement light and a distance to an object to be observed is acquired on the basis of the position of a spot of the auxiliary measurement light captured in an image obtained by the image pickup optical system.

SUMMARY OF THE INVENTION

However, since a surface from which the auxiliary measurement light is emitted is inclined with respect to the distal end surface of the image pickup optical system in a case where auxiliary measurement light is obliquely emitted as in WO2018/051680A, unevenness is formed at the distal end part of an insertion part of the endoscope. For this reason, there is a problem, such as clogging caused by foreign matters occurring at an uneven portion.

The present invention has been made in consideration of the above-mentioned background, and an object of the present invention is to provide an endoscope and an endoscope apparatus that do not have unevenness at a distal end part of an insertion part of the endoscope.

An endoscope according to an aspect of the present invention comprises: a first hole portion and a second hole portion that are provided at a distal end of an insertion part; an image pickup optical system that is housed in the first hole portion; an auxiliary measurement light optical system that is housed in the second hole portion and emits auxiliary measurement light, of which an optical axis is inclined with respect to an optical axis of the image pickup optical system, toward the optical axis of the image pickup optical system from a light-emitting surface thereof disposed in the second hole portion; and a transparent member that includes a flat surface flush with the distal end of the insertion part and is inserted into an optical path of the auxiliary measurement light emitted from the light-emitting surface.

It is preferable that the transparent member functions as a lid closing the second hole portion.

It is preferable that the transparent member includes a close contact surface being in close contact with the light-emitting surface and a space between the close contact surface and the flat surface on the optical path of the auxiliary measurement light is made airtight by the transparent member.

It is preferable that the transparent member includes an optical member and the close contact surface is formed on the optical member.

It is preferable that the transparent member includes a transparent filling material filled between the close contact surface and the flat surface and the filling material is in close contact with the light-emitting surface, so that the close contact surface is formed.

It is preferable that an optical refractive index of a medium positioned on one side of the light-emitting surface close to the auxiliary measurement light optical system among mediums positioned on the optical path of the auxiliary measurement light is lower than an optical refractive index of a medium positioned on the other side thereof close to the transparent member.

It is preferable that the optical axis of the image pickup optical system and the optical axis of the auxiliary measurement light optical system cross each other.

It is preferable that a distance between the distal end of the insertion part and an intersection between the optical axis of the image pickup optical system and the optical axis of the auxiliary measurement light optical system is in a range of 8 mm or more and 12 mm or less.

It is preferable that the auxiliary measurement light is linear parallel light.

Further, an endoscope apparatus according to another aspect of the present invention comprises the above-mentioned endoscope, a position specifying section that specifies a position of a specific region formed by the auxiliary measurement light from a region included in a picked-up image obtained by the image pickup optical system, and a display control unit that causes a display unit to display a specific image in which a measurement marker set according to the position of the specific region is displayed in the picked-up image.

According to the present invention, it is possible to provide an endoscope and an endoscope apparatus not having a problem, such as clogging caused by foreign matters occurring at an uneven portion of a distal end part of the insertion part.

DESCRIPTION OF THE PREFERRED EMBODIMENTS

Figure 1:
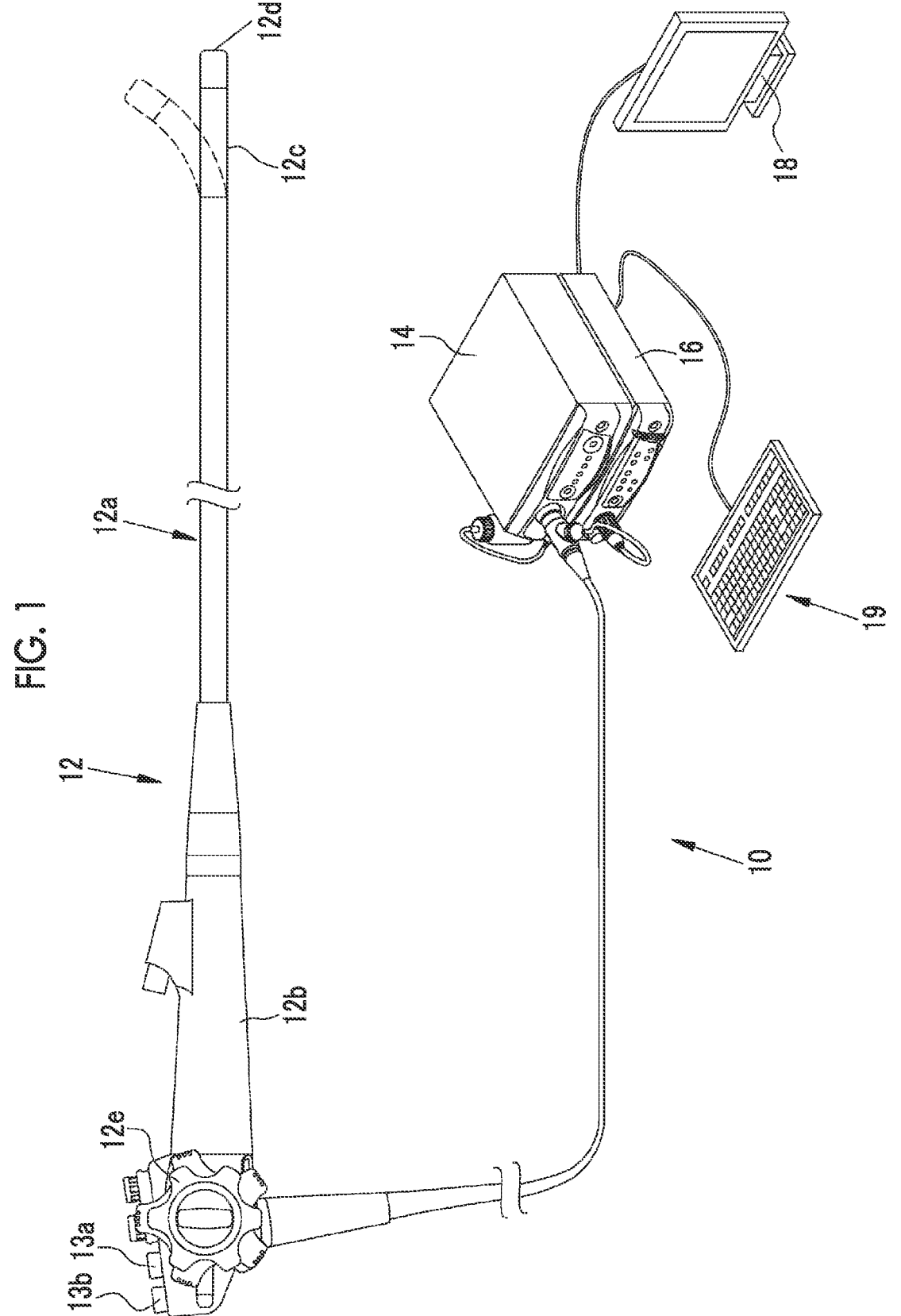
FIG. 1 is a diagram showing the appearance of an endoscope apparatus.

As shown in FIG. 1, an endoscope apparatus 10 includes an endoscope 12, a light source device 14, a processor device 16, a monitor 18, and a user interface 19. The endoscope 12 is optically connected to the light source device 14, and is electrically connected to the processor device 16. The processor device 16 is electrically connected to the monitor 18 (display unit) that displays an image. The user interface 19 is connected to the processor device 16, and is used for various setting operations and the like for the processor device 16. The user interface 19 includes a mouse and the like in addition to a keyboard shown in FIG. 1.

The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. The bendable part 12c operates to be bent by the operation of angle knobs 12e of the operation part 12b. The distal end part 12d is made to face in a desired direction by the bending operation of the bendable part 12c.

The endoscope 12 has a normal mode and a length measurement mode, and these two modes are switched by a mode changeover switch 13a that is provided on the operation part 12b of the endoscope 12. The normal mode is a mode where an object to be observed is illuminated with illumination light. In the length measurement mode, an object to be observed is illuminated with illumination light or auxiliary measurement light and a measurement marker (see FIGS. 11 to 13) to be used to measure the size and the like of the object to be observed is displayed in a picked-up image obtained from the image pickup of the object to be observed. The auxiliary measurement light is light that is used to measure a subject. The endoscope 12 may have a special light mode where a subject is illuminated with special light, which is used to emphasize a specific portion, as illumination light, and the like in addition to the normal mode and the length measurement mode.

The operation part 12b of the endoscope 12 is provided with a freeze switch 13b that is used to give a static image-acquisition instruction to acquire the static image of a picked-up image. In a case where a user operates the freeze switch 13b, the screen of the monitor 18 is frozen and displayed and an alert sound (for example, "beep") informing the acquisition of a static image is generated together. Then, the static images of the picked-up image, which are obtained before and after the operation timing of the freeze switch 13b, are stored in a static image storage unit 42 (see FIG. 3) provided in the processor device 16 (see FIG. 3). The measurement marker may also be stored together with the static image of the picked-up image in a case where the endoscope 12 is set to the length measurement mode.

The static image storage unit 42 is a storage unit, such as a hard disk or a universal serial bus (USB) memory. In a case where the processor device 16 can be connected to a network, the static image of the picked-up image may be stored in a static image storage server (not shown), which is connected to the network, instead of or in addition to the static image storage unit 42.

A static image-acquisition instruction may be given using an operation device other than the freeze switch 13b. For example, a foot pedal may be connected to the processor device 16, and a static image-acquisition instruction may be given in a case where a user operates the foot pedal (not shown) with a foot. A static image-acquisition instruction may be given by a foot pedal that is used to switch a mode. Further, a gesture recognition unit (not shown), which recognizes the gestures of a user, may be connected to the processor device 16, and a static image-acquisition instruction may be given in a case where the gesture recognition unit recognizes a specific gesture of a user. The gesture recognition unit may also be used to switch a mode.

Further, a sight line input unit (not shown), which is provided close to the monitor 18, may be connected to the processor device 16, and a static image-acquisition instruction may be given in a case where the sight line input unit recognizes that a user's sight line is in a predetermined region of the monitor 18 for a predetermined time or longer. Furthermore, a voice recognition unit (not shown) may be connected to the processor device 16, and a static image-acquisition instruction may be given in a case where the voice recognition unit recognizes a specific voice generated by a user. The voice recognition unit may also be used to switch a mode. Moreover, an operation panel (not shown), such as a touch panel, may be connected to the processor device 16, and a static image-acquisition instruction may be given in a case where a user performs a specific operation on the operation panel. The operation panel may also be used to switch a mode.

Figure 2:
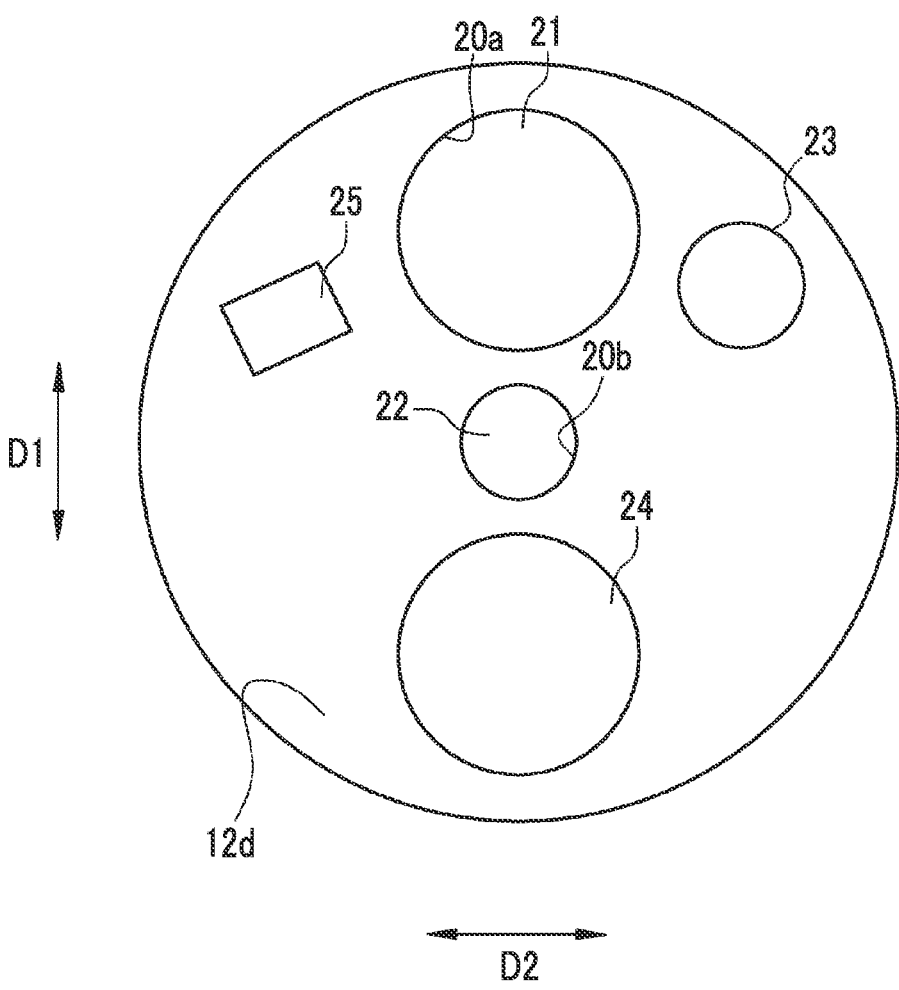
FIG. 2 is a plan view of a distal end of an insertion part of an endoscope.

As shown in FIG. 2, the distal end part 12d has a substantially circular shape, and is provided with a first hole portion 20a and a second hole portion 20b. An image pickup optical system 29b (see FIG. 3) of the endoscope 12 is housed in the first hole portion 20a, and an objective lens 21, which is positioned closest to a subject among components of the image pickup optical system 29b, is exposed to the first hole portion 20a. An auxiliary measurement light optical system 30 (see FIG. 3) of the endoscope 12 is housed in the second hole portion 20b. A transparent lid 22 (transparent member) is provided at the distal end of the second hole portion 20b and the second hole portion 20b is closed by the transparent lid 22, so that the auxiliary measurement light optical system 30 is housed behind the transparent lid 22.

Further, the distal end part 12*d* of the endoscope is provided with an illumination lens 23 that is used to illuminate a subject with illumination light, an opening 24 that allows a treatment tool to protrude toward a subject, and an air/water supply nozzle 25 that is used to supply air and water.

An optical axis Ax (see FIG. 4) of the objective lens 21 (which is the optical axis of the image pickup optical system 29*b* and will be referred to as an image pickup optical axis hereinafter) extends in a direction perpendicular to the plane of paper of FIG. 2. That is, the image pickup optical axis Ax is orthogonal to both a vertical first direction D1 and a horizontal second direction D2 orthogonal to each other. The objective lens 21 (first hole portion 20*a*) and the transparent lid 22 (second hole portion 20*b*) are arranged in the first direction D1.

Figure 3:
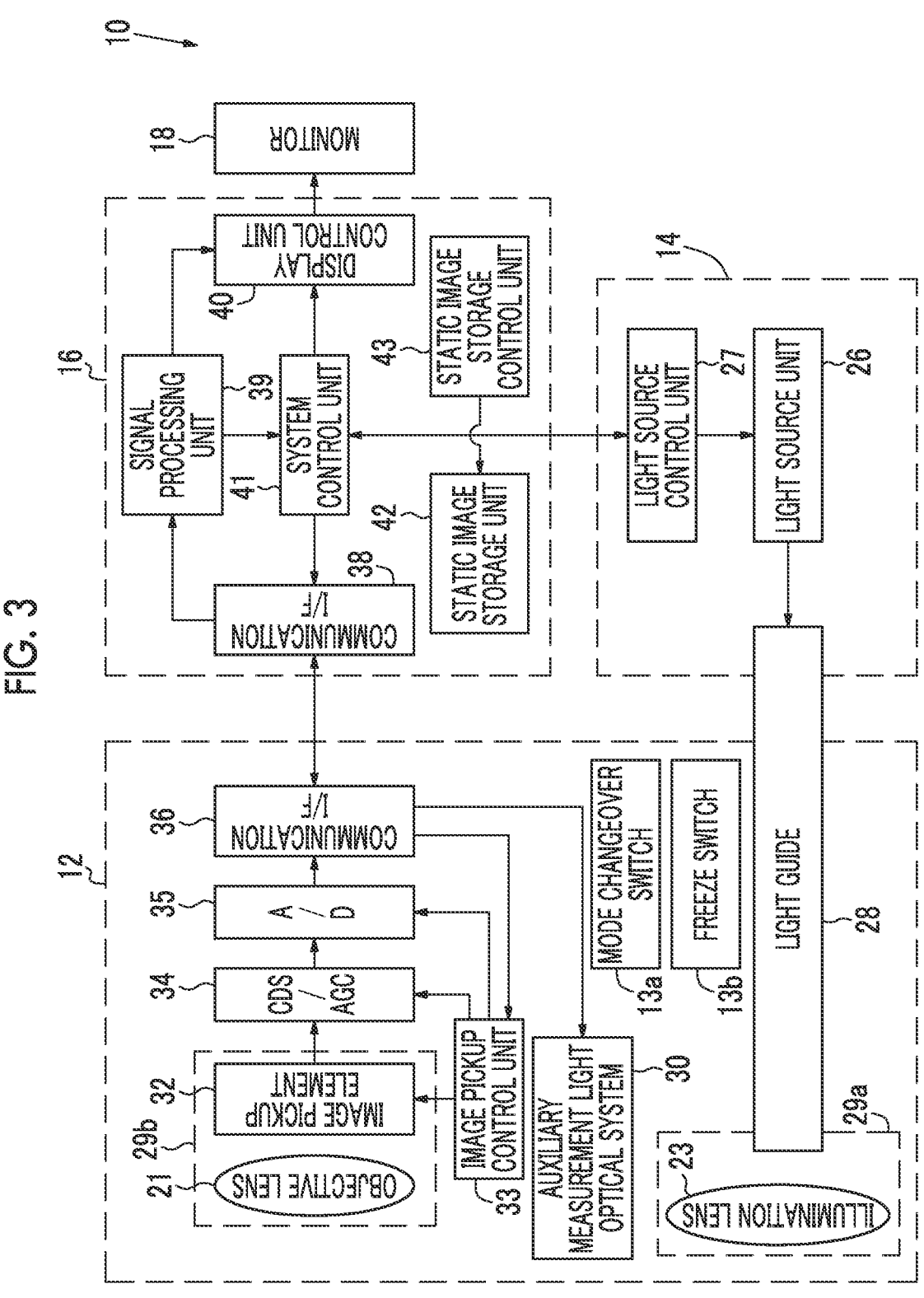
FIG. 3 is a block diagram showing the functions of the endoscope apparatus.

As shown in FIG. 3, the light source device 14 comprises a light source unit 26 and a light source control unit 27. The light source unit 26 generates illumination light that is used to illuminate a subject. Illumination light emitted from the light source unit 26 is incident on a light guide 28, and a subject is irradiated with illumination light through the illumination lens 23. It is preferable that a white light source emitting white light, a plurality of light sources, which include a white light source and a light source emitting another color light (for example, a blue light source emitting blue light), or the like is used as a light source of the illumination light in the light source unit 26. The light source control unit 27 is connected to a system control unit 41 of the processor device 16. The light source control unit 27 controls the light source unit 26 on the basis of an instruction given from the system control unit 41. The system control unit 41 not only gives an instruction related to light source control to the light source control unit 27 but also controls a light source 30*a* (see FIG. 4) of the auxiliary measurement light optical system 30.

The distal end part 12*d* of the endoscope 12 is provided with an illumination optical system 29*a*, an image pickup optical system 29*b*, and the auxiliary measurement light optical system 30. The illumination optical system 29*a* includes the illumination lens 23, and an object to be observed is irradiated with light, which is emitted from the light guide 28, through the illumination lens 23. The image pickup optical system 29*b* includes the objective lens 21 and an image pickup element 32. Light reflected from the object to be observed is incident on the image pickup element 32 through the objective lens 21. Accordingly, the reflected image of the object to be observed is formed on the image pickup element 32.

The image pickup element 32 is a color image pickup sensor, and picks up the reflected image of an object to be examined and outputs image signals. It is preferable that the image pickup element 32 is a charge coupled device (CCD) image pickup sensor, a complementary metal-oxide semiconductor (CMOS) image pickup sensor, or the like. The image pickup element 32 used in an embodiment of the present invention is a color image pickup sensor that is used to obtain RGB image signals corresponding to three colors of R (red), G (green), and B (blue). The image pickup element 32 is controlled by an image pickup control unit 33. A complementary color image pickup element, which is provided with color filters corresponding to complementary colors, that is, C (cyan), M (magenta), Y (yellow), and G (green), may be used as the image pickup element 32.

Image signals output from the image pickup element 32 are transmitted to a CDS/AGC circuit 34. The CDS/AGC circuit 34 performs correlated double sampling (CDS) or auto gain control (AGC) on the image signals that are analog signals. The image signals, which have been transmitted through the CDS/AGC circuit 34, are converted into digital image signals by an analog/digital converter (A/D converter) 35. The digital image signals, which have been subjected to A/D conversion, are input to the processor device 16 through a communication interface (I/F) 36.

The processor device 16 comprises a communication interface (I/F) 38 that is connected to the communication I/F 36 of the endoscope 12, a signal processing unit 39, a display control unit 40, and the system control unit 41. The communication I/F receives the image signals, which are transmitted from the communication I/F 36 of the endoscope 12, and transmits the image signals to the signal processing unit 39. A memory, which temporarily stores the image signals received from the communication I/F 38, is built in the signal processing unit 39, and the signal processing unit 39 processes an image signal group, which is a set of the image signals stored in the memory, to generate the picked-up image.

In a case where the endoscope 12 is set to the length measurement mode, the signal processing unit 39 may be adapted to perform structure-emphasis processing of emphasizing structures, such as blood vessels, or color difference-emphasis processing of increasing a color difference between a normal area and a lesion area of the object to be observed on the picked-up image. Further, the signal processing unit 39 and the system control unit 41 may be provided in an external processing device (not shown) connected to the processor device 16, and processing related to the signal processing unit 39 and the system control unit 41 may be performed by the external processing device. For example, in a case where the endoscope 12 is set to the length measurement mode, a first picked-up image including a spot SP may be sent to the external processing device and the position of the spot SP may be specified from the first picked-up image by the external processing device. Further, the external processing device may set a measurement marker according to the position of the spot SP (see FIGS. 11 to 13) and may generate a specific image in which the set measurement marker is displayed in the first picked-up image. The generated specific image is transmitted to the processor device 16.

The display control unit 40 causes the monitor 18 to display the picked-up image that is generated by the signal processing unit 39. The system control unit 41 performs the control of the image pickup element 32 through the image pickup control unit 33 provided in the endoscope 12. The image pickup control unit 33 also performs the control of the CDS/AGC circuit 34 and the A/D converter 35 together with the control of the image pickup element 32. A static image storage control unit 43 performs control related to the static image of the picked-up image to be stored in the static image storage unit 42.

Figure 4:
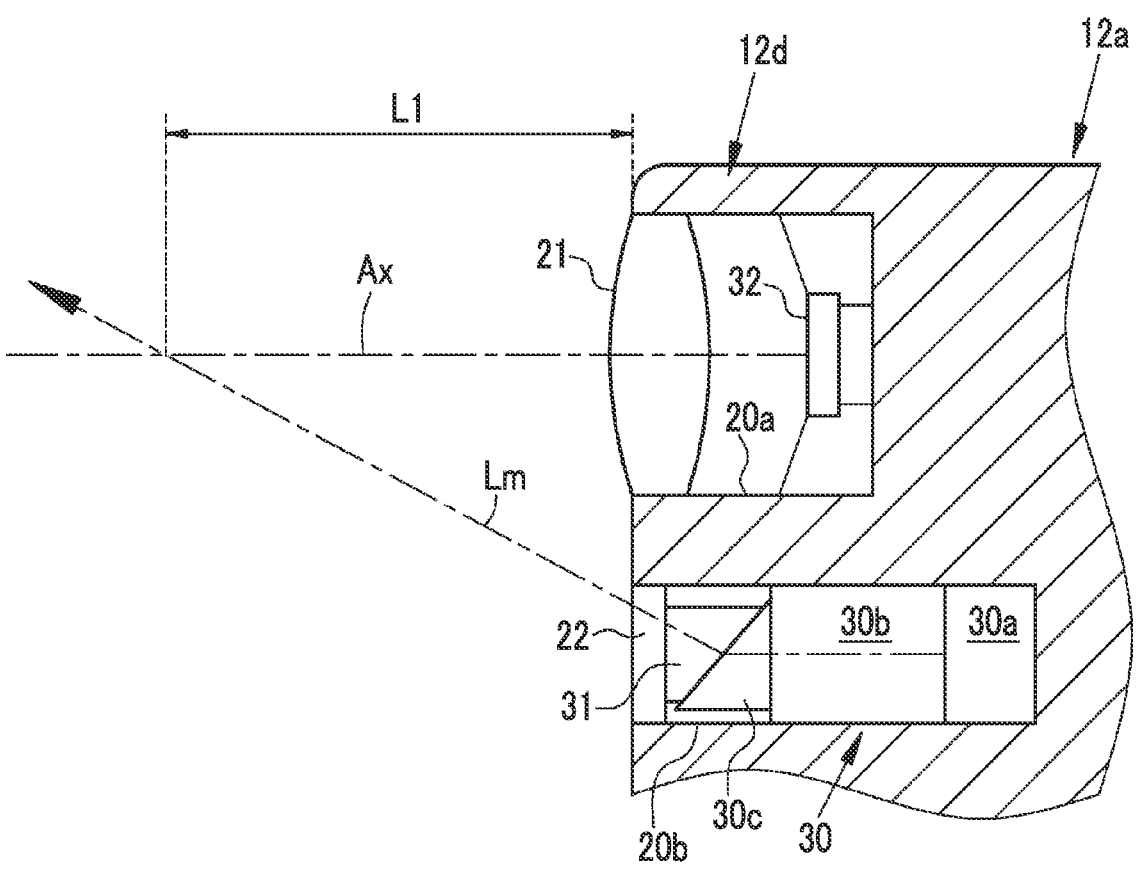
FIG. 4 is a diagram illustrating an auxiliary measurement light optical system.
Figure 5:
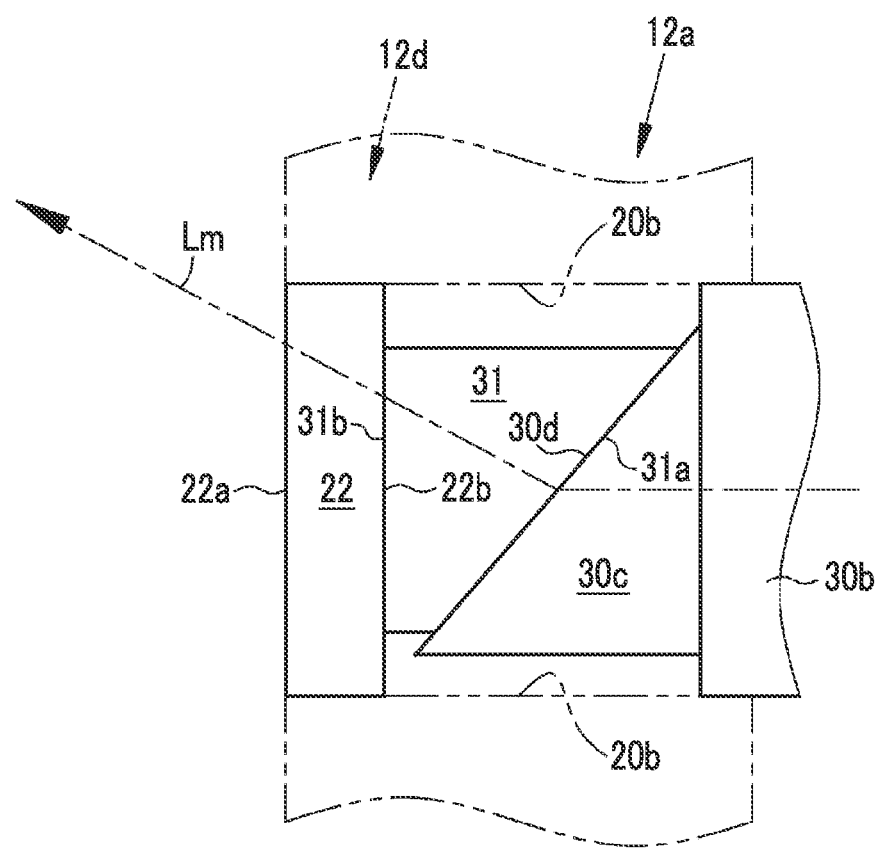
FIG. 5 is a diagram illustrating the auxiliary measurement light optical system.

As shown in FIGS. 4 and 5, the auxiliary measurement light optical system 30 comprises a light source 30*a*, an auxiliary measurement light-generating element 30*b* (a collimator lens, a diffractive optical element (DOE), or the like), and a prism 30*c*, and the light source 30*a*, the auxiliary measurement light-generating element 30*b*, and the prism 30*c* are housed in the second hole portion 20*b*. The light source 30*a* is to emit light having a color that can be detected by pixels of the image pickup element 32 (specifically visible light), and includes a light-emitting element, such as a laser light source (laser diode (LD)) or a light emitting diode (LED), and an emission lens.

It is preferable that the light emitted from the light source 30*a* is, for example, red light having a wavelength of 600 nm or more and 650 nm or less. Alternatively, green light having a wavelength of 495 nm or more and 570 nm or less may be used. The light source 30a is controlled by the system control unit 41 and emits light on the basis of an instruction given from the system control unit 41. The auxiliary measurement light-generating element 30b converts the light, which is emitted from the light source, into auxiliary measurement light that is used to measure a subject. The auxiliary measurement light, which is converted in this way, is linear parallel light that is collimated (of which the diffusion and convergence are suppressed).

The prism 30c bends (inclines) the optical axis Lm of the auxiliary measurement light (hereinafter, referred to as an auxiliary light optical axis) to change the travel direction of the auxiliary measurement light. Since a light-emitting surface 30d of the prism 30c is inclined with respect to the distal end surface of the insertion part 12a (distal end part 12d), the prism 30c inclines the auxiliary light optical axis Lm with respect to the image pickup optical axis Ax so that the auxiliary light optical axis Lm crosses the visual field of the image pickup optical system 29b including the objective lens 21 and lens groups. In this embodiment, the prism 30c inclines the auxiliary light optical axis Lm so that the auxiliary light optical axis Lm crosses the image pickup optical axis Ax in a range where a distance L1 from the distal end (distal end surface) of the insertion part 12a is in a range of 8 mm or more and 12 mm or less. Then, a subject is irradiated with the auxiliary measurement light inclined in this way, so that a spot SP (see FIGS. 11 to 13) as a circular region (specific region) is formed on the subject. The position of the spot SP is specified by a position specifying section 50 and a measurement marker showing an actual size is set according to the position of the spot SP. The set measurement marker is displayed in the picked-up image.

As described above, the auxiliary measurement light optical system 30 is housed in the second hole portion 20b and the light-emitting surface 30d of the prism 30c, which is the distal end of the auxiliary measurement light optical system 30, is inclined with respect to the distal end surface of the insertion part 12a. Accordingly, a portion of the light-emitting surface 30d is recessed from the distal end surface of the insertion part 12a. For this reason, in order to make the distal end surface of the insertion part 12a flat, the transparent lid 22 is provided in the endoscope 12 to close the second hole portion 20b. The transparent lid 22 is formed in the shape of a plate, and one end surface (surface) of the transparent lid 22 is formed of a flat surface 22a. Then, the transparent lid 22 is disposed so that the flat surface 22a is flush with the distal end of the second hole portion 20b (the distal end surface of the insertion part 12a). Since the distal end surface of the insertion part 12a is made flat in this way, it is possible to prevent a problem, such as the blocking of the auxiliary measurement light occurring since the distal end surface is clogged by foreign matters in a case where the transparent lid 22 is not provided.

The flat surface 22a includes not only a completely flat surface without unevenness but also a substantially flat surface, specifically, a surface on which fine unevenness of 0.1 mm or less is present. Further, the flat surface 22a also includes a curved surface. However, in a case where the flat surface 22a is a curved surface, it is preferable that the flat surface 22a is a gently curved surface of which the inclination of a tangent is continuous in a range where a height is 1 mm or less. Furthermore, for example, from the comparison of a case where the flat surface 22a is curved in a convex shape and a case where the flat surface 22a is curved in a concave shape, a problem that the auxiliary measurement light is blocked is less likely to be generated (the clogging of the flat surface 22a caused by foreign matters is less likely to occur) in the case where the flat surface 22a is curved in a convex shape. For this reason, in a case where the flat surface 22a is a curved surface, it is preferable that the flat surface 22a is curved in a convex shape as a whole.

In addition, a case where the transparent lid 22 (flat surface 22a) is flush with the distal end of the second hole portion 20b (the distal end surface of the insertion part 12a) includes not only a case where these two portions are connected to each other so as to be completely flush with each other without a level difference but also a case where the two portions are substantially flush with each other, specifically, a slight level difference of 0.1 mm or less is present between the two portions. From the comparison of a case where the transparent lid 22 protrudes from the second hole portion 20b and a case where the transparent lid 22 is recessed from the second hole portion 20b, a problem that the auxiliary measurement light is blocked is less likely to be generated (the clogging of the flat surface 22a caused by foreign matters is less likely to occur) in the case where the transparent lid 22 protrudes from the second hole portion 20b. For this reason, in a case where a level difference is present between the second hole portion 20b and the transparent lid 22, it is preferable that the transparent lid 22 protrudes from the second hole portion 20b.

In FIG. 5, a prism 31 (a transparent member, an optical member) is disposed between the transparent lid 22 and the light-emitting surface 30d. The prism 31 includes a first close contact surface 31a (close contact surface) and a second close contact surface 31b, the first close contact surface 31a is in close contact with the light-emitting surface 30d, and the second close contact surface 31b is in close contact with a back 22b of the transparent lid 22. Gas is removed from a space between the transparent lid 22 and the light-emitting surface 30d by the prism 31, so that the space between the transparent lid 22 and the light-emitting surface 30d is made airtight. Since the space between the transparent lid 22 and the light-emitting surface 30d is made airtight as described above, the generation of a problem caused by condensation can be prevented. That is, since condensation does not occur on the back 22b (a surface opposite to the flat surface 22a) of the transparent lid 22 and/or the light-emitting surface 30d, problems, such as the attenuation, diffusion, convergence, and/or refraction of the auxiliary measurement light, (problems caused by condensation) are not generated.

Figure 6:
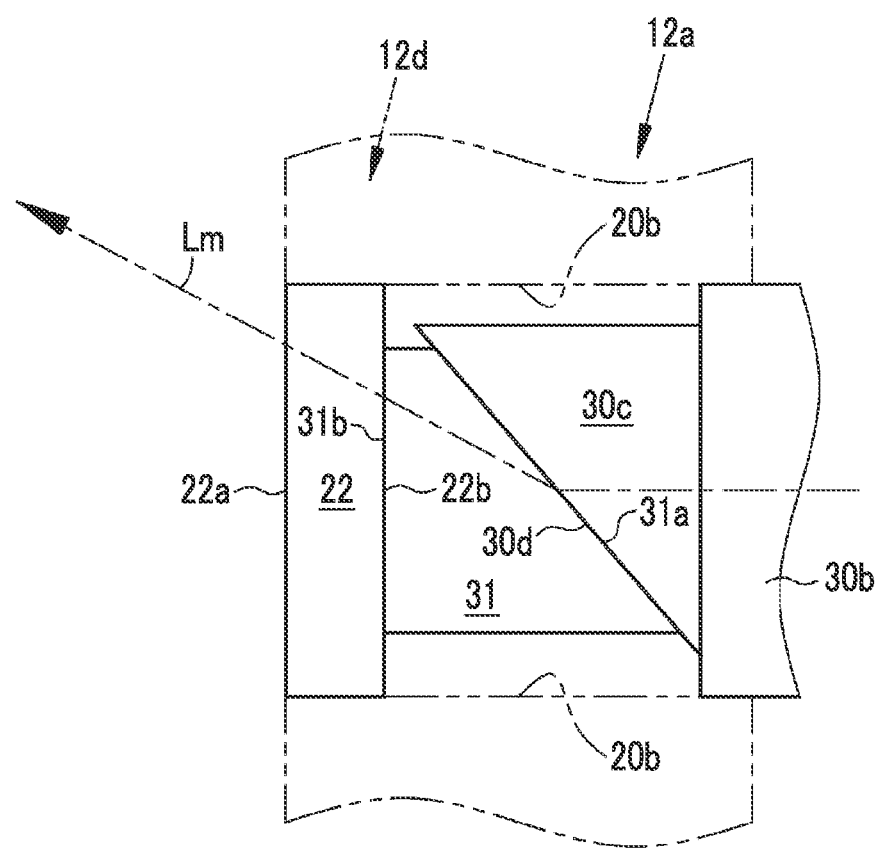
FIG. 6 is a diagram illustrating an auxiliary measurement light optical system.

The present invention is not limited to the embodiment, and the detailed configuration thereof can be appropriately changed. For example, configuration (see FIG. 5) where "n1<n2" is satisfied, in a case where the refractive index of the prism 30c (the refractive index of a medium positioned on one side of the light-emitting surface 30d close to an auxiliary measurement light source) is denoted by "n1" and the refractive index of the prism 31 (the refractive index of a medium positioned on the other side of the light-emitting surface 30d close to the transparent member) is denoted by "n2", and the light-emitting surface 30d is inclined toward the image pickup optical axis Ax has been described in the embodiment by way of example. However, configuration reverse to the configuration shown in FIG. 5 may be provided. Specifically, as shown in FIG. 6, "n1>n2" may be satisfied and the light-emitting surface 30d may be inclined toward a side opposite to the image pickup optical axis Ax. However, in a case where the configuration shown in FIG. 5 and the configuration shown in FIG. 6 are compared with each other, there is a risk that auxiliary measurement light is totally reflected on the light-emitting surface 30_d_ in the configuration shown in FIG. 6. The inclination of the light-emitting surface 30_d_ (an angle at which the auxiliary measurement light is bent) is limited for the avoidance of this risk. In contrast, since there is no risk that the auxiliary measurement light is totally reflected on the light-emitting surface 30_d_ in the configuration shown in FIG. 5, there is no limitation as in the configuration of FIG. 6. Accordingly, the configuration shown in FIG. 5 is preferable between the configuration shown in FIG. 5 and the configuration shown in FIG. 6. The same members as those of the above-mentioned embodiment (see FIGS. 4 and 5) will be denoted in FIG. 6 and FIGS. 7 and 8 to be described later by the same reference numerals as those of the above-mentioned embodiment, and the description thereof will be omitted.

Figure 7:
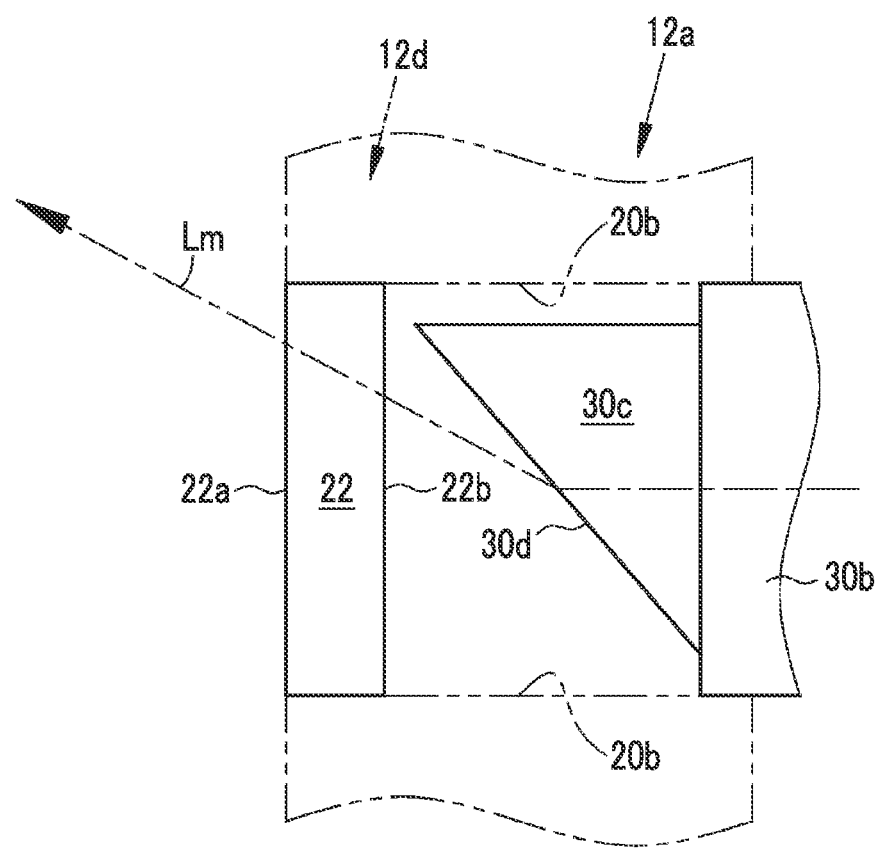
FIG. 7 is a diagram illustrating an auxiliary measurement light optical system.

Further, a space between the transparent lid 22 and the light-emitting surface 30_d_ may be a space in which a member is not disposed (a space filled with gas) as shown in FIG. 7. However, in this case, there is a risk that problems caused by condensation are generated as described above. For this reason, it is preferable that the space between the transparent lid 22 and the light-emitting surface 30_d_ is made airtight (see FIGS. 5 and 6).

In order to prevent the generation of the problems caused by condensation, the entire area between the transparent lid 22 and the light-emitting surface 30_d_ does not need to be made airtight and a portion positioned on the optical path of the auxiliary measurement light has only to be airtight. For this reason, the shape and/or size of the prism 31 can be appropriately changed in a range that satisfies this (in a range satisfying a condition that at least a portion positioned on the optical path of the auxiliary measurement light is made airtight).

Figure 8:
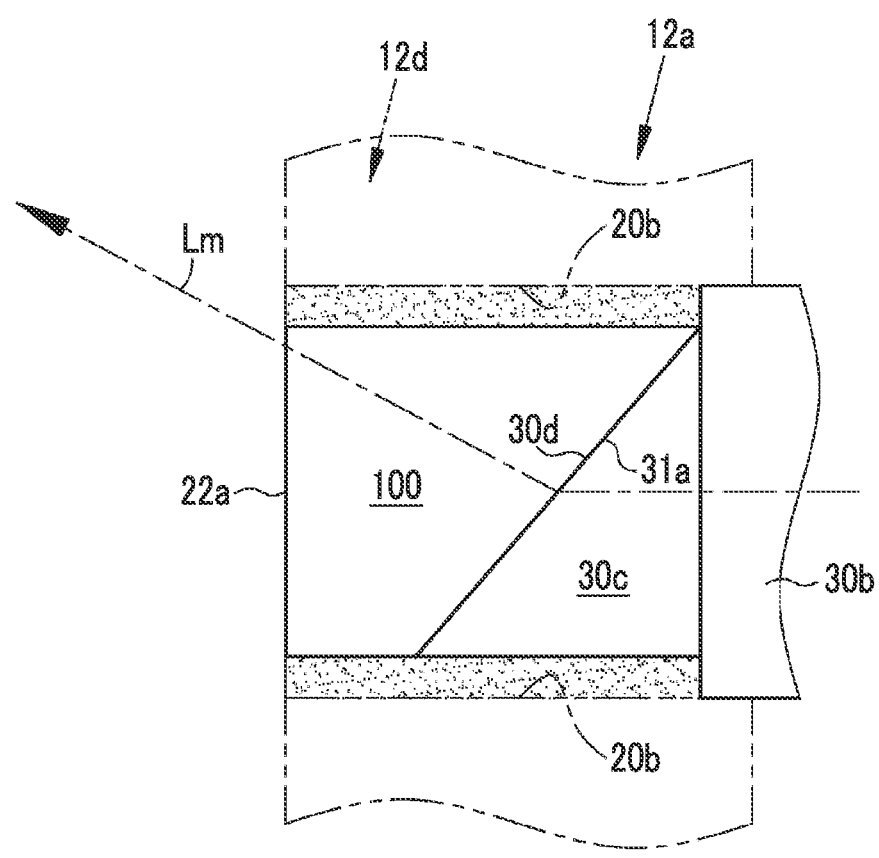
FIG. 8 is a diagram illustrating an auxiliary measurement light optical system.

An example where the transparent lid 22 and the prism 31 are separately provided has been described, but the transparent lid 22 and the prism 31 may be made of a common material so as to be integrated with each other as shown in FIG. 8. In the example shown in FIG. 8, a prism 100 is provided instead of the transparent lid 22 (see FIG. 5) and the prism 31 (see FIG. 5). The prism 100 includes the same flat surface 22_a_ as the transparent lid 22. Further, the prism 100 includes the same first close contact surface 31_a_ as the prism 31. Furthermore, gaps between the prisms 100 and 30_c_ and the second hole portion 20_b_ are filled with an adhesive as shown by hatching in FIG. 8 in the example shown in FIG. 8, so that the distal end surface of the insertion part 12_a_ is made flat.

Moreover, a transparent filling material, such as an adhesive, may be filled between the transparent lid 22 and the light-emitting surface 30_d_ as a transparent member instead of the prism 31 (see FIG. 5) to make a portion positioned on the optical path of the auxiliary measurement light airtight. In addition, a transparent filling material may be filled in the second hole portion 20_b_ instead of the prism 31 (see FIG. 5) and the transparent lid 22 (see FIG. 5) to make a portion positioned on the optical path of the auxiliary measurement light airtight and to form the distal end surface of the insertion part 12_a_ as a flat surface.

Further, the auxiliary measurement light optical system 30 has only to be capable of emitting auxiliary measurement light toward the visual field of the image pickup optical system. For example, the light source 30_a_ may be provided in the light source device and light emitted from the light source 30_a_ may be guided to the auxiliary measurement light-generating element 30_b_ by optical fibers. Furthermore, the prism 30_c_ may not be used and the directions of the light source 30_a_ and the auxiliary measurement light-generating element 30_b_ may be inclined with respect to the image pickup optical axis Ax so that auxiliary measurement light is emitted in a direction crossing the visual field of the image pickup optical system. Even in this case, a light-emitting surface in a case where auxiliary measurement light is emitted from the auxiliary measurement light optical system 30 is inclined with respect to and recessed from the distal end surface of the insertion part 12_a_. Accordingly, in a case where a transparent member is provided to form the distal end surface of the insertion part 12_a_ as a flat surface, it is possible to prevent a problem, such as the blocking of the auxiliary measurement light occurring since the distal end surface is clogged by foreign matters.

The refraction of the auxiliary measurement light occurs not only in a case where the auxiliary measurement light passes through the light-emitting surface 30_d_ but also in a case where the auxiliary measurement light is emitted from the transparent member. Further, in a case where the transparent member is composed of the transparent lid 22 and the prism 31 (see FIGS. 5 and 7) and the materials of the transparent member are different from each other depending on portions, the refraction of the auxiliary measurement light occurs even in a case where the auxiliary measurement light passes through a boundary between the materials. For this reason, an actual product is naturally designed in consideration of even the refraction of the auxiliary measurement light occurring in these cases. However, in this specification, in order to avoid the complication of description, description is made without the consideration of the refraction of the auxiliary measurement light occurring in these cases (refraction other than the refraction of the auxiliary measurement light occurring in a case where the auxiliary measurement light passes through the light-emitting surface 30_d_).

Figure 9:
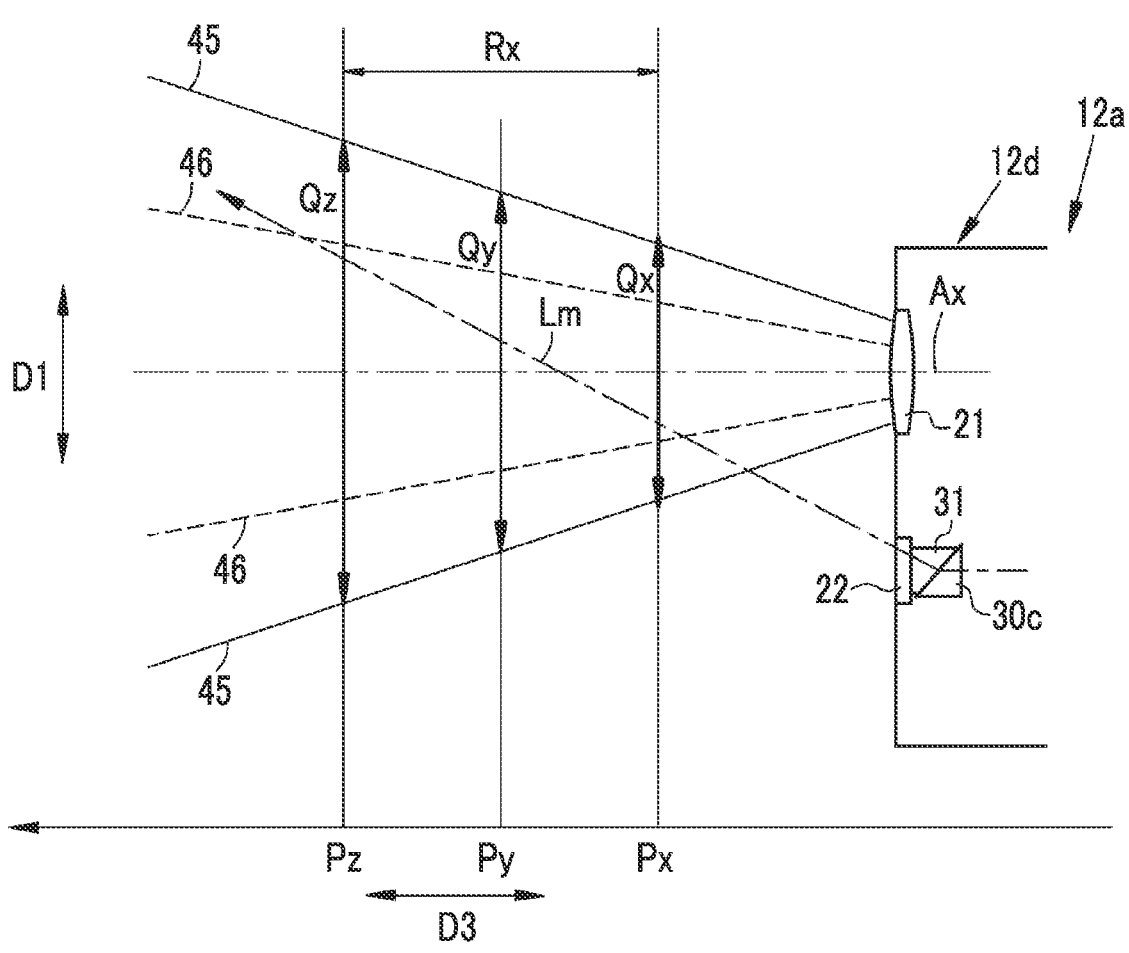
FIG. 9 is a diagram illustrating a relationship between the distal end of the insertion part of the endoscope and a near end Px, an intermediate vicinity Py, and a far end Pz in a range Rx of an observation distance.

As shown in FIG. 9, the auxiliary light optical axis Lm of the auxiliary measurement light is inclined with respect to the image pickup optical axis Ax so that the auxiliary light optical axis Lm crosses the image pickup optical axis Ax. In a case where a subject can be observed in a range Rx of an observation distance, it is understood that the positions (points where the respective arrows Qx, Qy, and Qz cross the image pickup optical axis Ax) of the spot SP, which is formed on the subject by the auxiliary measurement light, in image pickup ranges (shown by arrows Qx, Qy, and Qz) at a near end Px, an intermediate vicinity Py, and a far end Pz of the range Rx are different from each other. The image pickup angle of view of the image pickup optical system is represented by a region between two solid lines 45, and measurement is performed in a central region (a region between two dotted lines 46), in which an aberration is small, of this image pickup angle of view.

Since the auxiliary light optical axis Lm is inclined as described above so that the auxiliary light optical axis Lm crosses the image pickup optical axis Ax, the size of the subject can be measured with a high accuracy. That is, the auxiliary light optical axis Lm may be inclined so as to cross the visual field of the image pickup optical system 29_b_ (the auxiliary light optical axis Lm does not need to necessarily cross the image pickup optical axis Ax). However, since the spot SP is formed in a region closer to a center of a picked-up image (a region where an aberration is smaller) in a case where the auxiliary light optical axis Lm crosses the image pickup optical axis Ax as compared to a case where the auxiliary light optical axis Lm does not cross the image pickup optical axis Ax, the sensitivity of the movement of the position of the spot to a change in an observation distance is higher. As a result, the size of the subject can be measured with a higher accuracy. Then, the image of the subject illuminated with the auxiliary measurement light is picked up by the image pickup element 32, so that a picked-up image including the spot SP is obtained. In the picked-up image, the position of the spot SP varies depending on a relationship between the image pickup optical axis Ax and the auxiliary light optical axis Lm and an observation distance. However, the number of pixels showing the same actual size (for example, 5 mm) is increased in the case of a short observation distance, and the number of pixels showing the same actual size is reduced in the case of a long observation distance.

Figure 10:
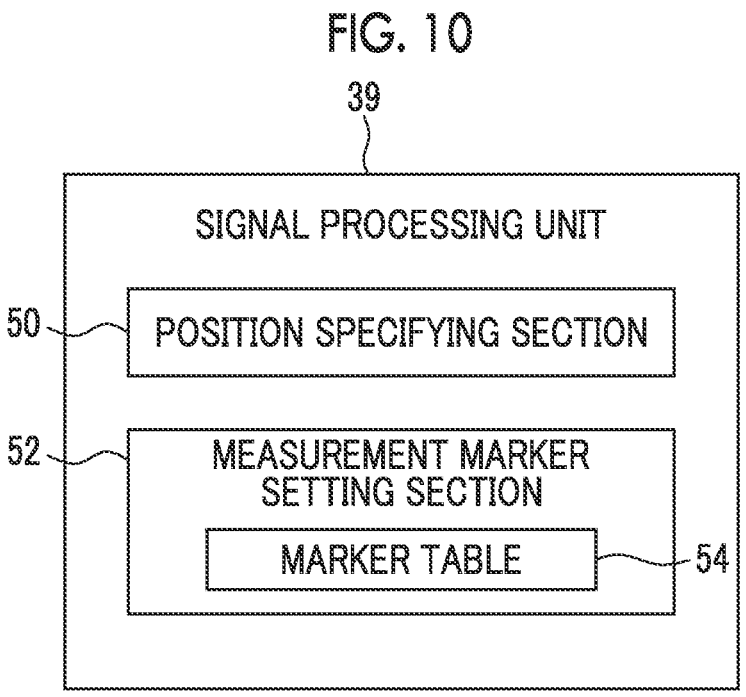
FIG. 10 is a block diagram showing the functions of a signal processing unit.

As shown in FIG. 10, the signal processing unit 39 of the processor device 16 comprises a position specifying section 50 and a measurement marker setting section 52 in order to recognize the position of the spot SP and to set a measurement marker. The position specifying section 50 specifies the position of the spot SP in a first picked-up image that is obtained from the image pickup of a subject illuminated with illumination light and auxiliary measurement light. The measurement marker setting section 52 sets a measurement marker on the basis of the position of the spot SP and generates a specific image in which the set measurement marker is displayed in the first picked-up image. The specific image is caused to be displayed on the monitor 18 by the display control unit 40. The specific image may be an image in which a measurement marker is set in a second picked-up image obtained from the image pickup of a subject illuminated with illumination light.

The position specifying section 50 specifies the position of the spot SP on the basis of the first picked-up image. Specifically, the position specifying section 50 specifies coordinate information about the position of the spot SP. The spot SP is displayed as a substantially circular red region that includes a large amount of components corresponding to the color of the auxiliary measurement light in the first picked-up image. Accordingly, the position specifying section 50 specifies the position of the spot SP from the substantially circular red region. As a method of specifying a position, for example, a picked-up image is binarized and the centroid of a white portion (pixel at which the signal intensity is higher than a threshold value for binarization) of a binarized image is specified as the position of the spot SP.

The measurement marker setting section 52 sets a measurement marker on the basis of the position of the spot SP in the first picked-up image. The measurement marker setting section 52 calculates the size of a marker from the position of the spot SP with reference to a marker table 54 in which a relationship between the position of the spot SP in the first picked-up image and the size of a measurement marker is stored. Then, the measurement marker setting section 52 sets a measurement marker corresponding to the size of the marker. After that, the measurement marker setting section 52 generates a specific image in which the measurement marker is superimposed and displayed in the first picked-up image.

Plural kinds of measurement markers, such as a first measurement marker and a second measurement marker, are included in the measurement marker, and a measurement marker to be displayed in the picked-up image among the plural kinds of measurement markers can be selected according to a user's instruction. For example, the user interface 19 is used for the user's instruction.

Figure 11:
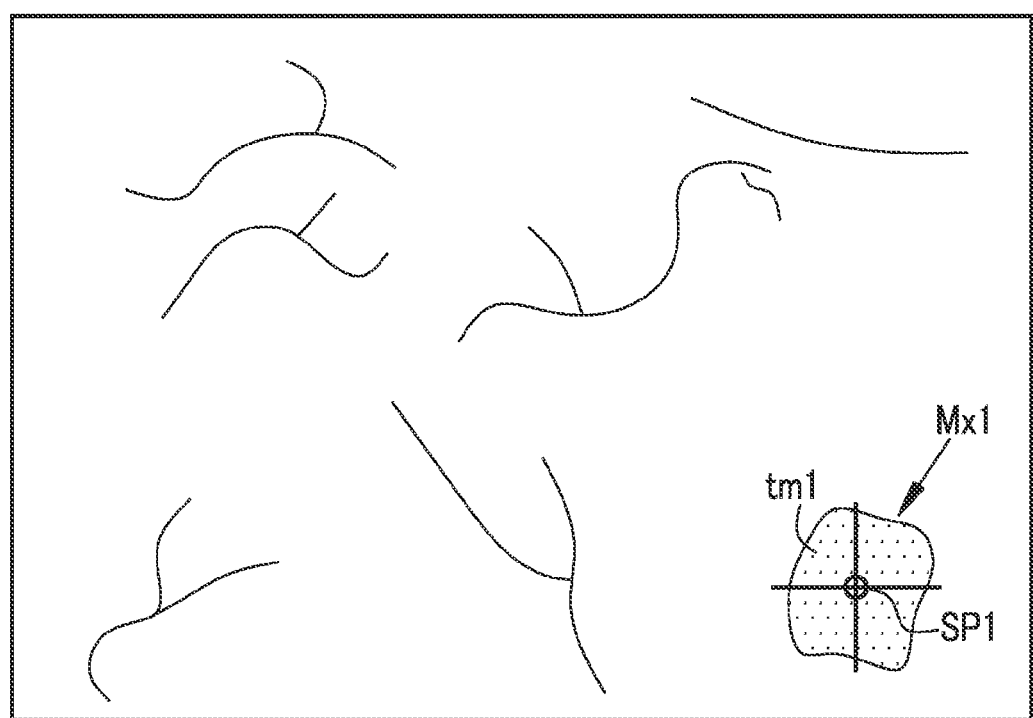
FIG. 11 is an image diagram showing a spot and a first measurement marker in a case where an observation distance corresponds to the near end Px.

For example, a cruciform measurement marker Mx is used as the first measurement marker. In this case, as shown in FIG. 11, a cruciform marker Mx1, which shows an actual size of 5 mm (a horizontal direction and a vertical direction of the picked-up image), is displayed at the center of a spot SP1 formed on a tumor tm1 of a subject in a case where an observation distance is close to the near end Px. Since the tumor tm1 and a range determined by the cruciform marker Mx1 substantially coincide with each other, the size of the tumor tm1 can be measured as about 5 mm.

Figure 12:
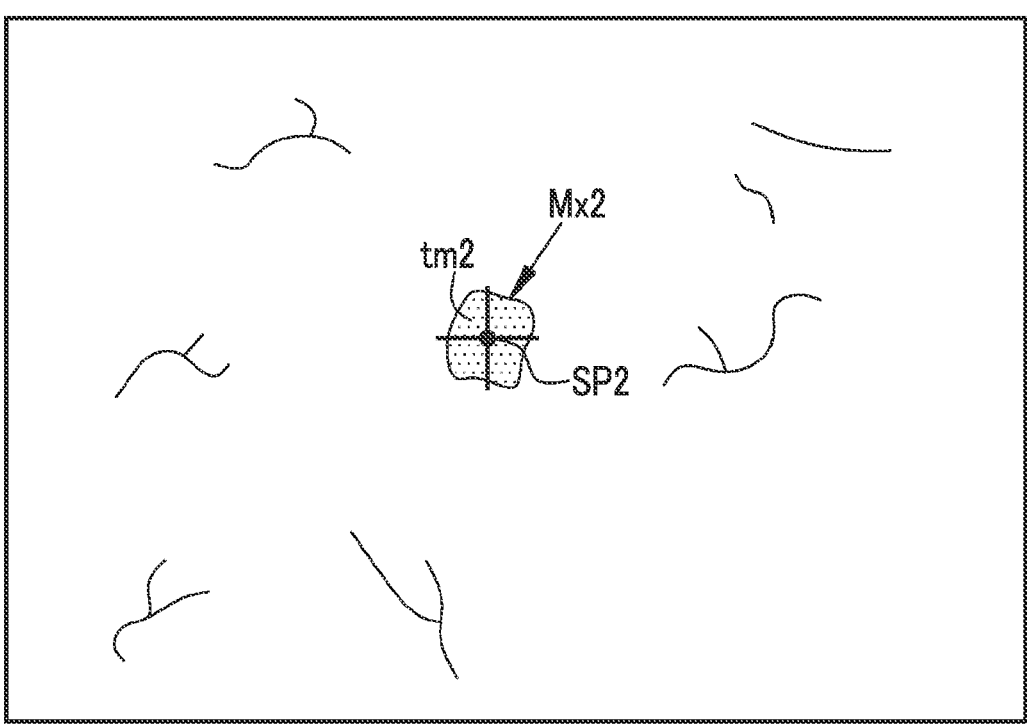
FIG. 12 is an image diagram showing a spot and a first measurement marker in a case where an observation distance corresponds to the intermediate vicinity Py.
Figure 13:
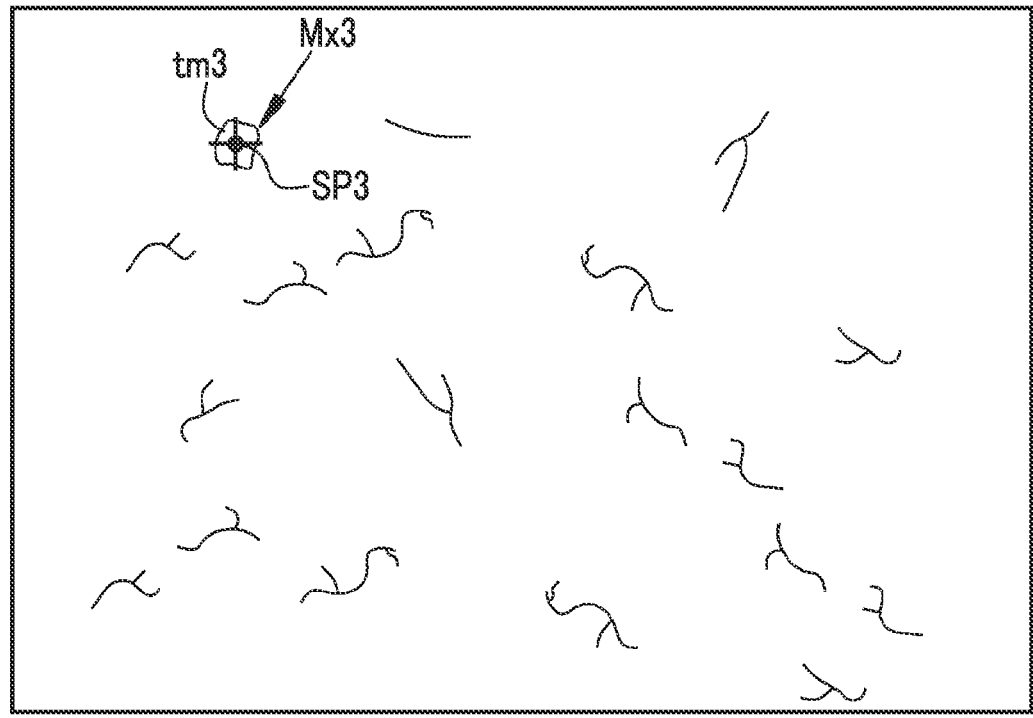
FIG. 13 is an image diagram showing a spot and a first measurement marker in a case where an observation distance corresponds to the far end Pz.

Likewise, as shown in FIG. 12, a cruciform marker Mx2, which shows an actual size of 5 mm (the horizontal direction and the vertical direction of the second picked-up image), is displayed at the center of a spot SP2 formed on a tumor tm2 of a subject in a case where an observation distance is close to the intermediate vicinity Py. Further, as shown in FIG. 13, a cruciform marker Mx3, which shows an actual size of 5 mm (the horizontal direction and the vertical direction of the second picked-up image), is displayed at the center of a spot SP3 formed on a tumor tm3 of a subject. Since the position of the spot on the image pickup surface of the image pickup element 32 varies depending on an observation distance as described above, a position where the marker is displayed also varies. As shown in FIGS. 11 to 13 having been described above, the size of the first measurement marker Mx corresponding to the same actual size of 5 mm is reduced with an increase in an observation distance.

In FIGS. 11 to 13, the center of the spot SP and the center of the marker are displayed to coincide with each other. However, the first measurement marker may be displayed at a position away from the spot SP in a case where there is no problem in measurement accuracy. Even in this case, it is preferable that the first measurement marker is displayed near the spot. Further, the distorted first measurement marker is not displayed, and the distortion of the picked-up image may be corrected so that an undistorted first measurement marker may be displayed in a corrected picked-up image.

Figures 14, 15:
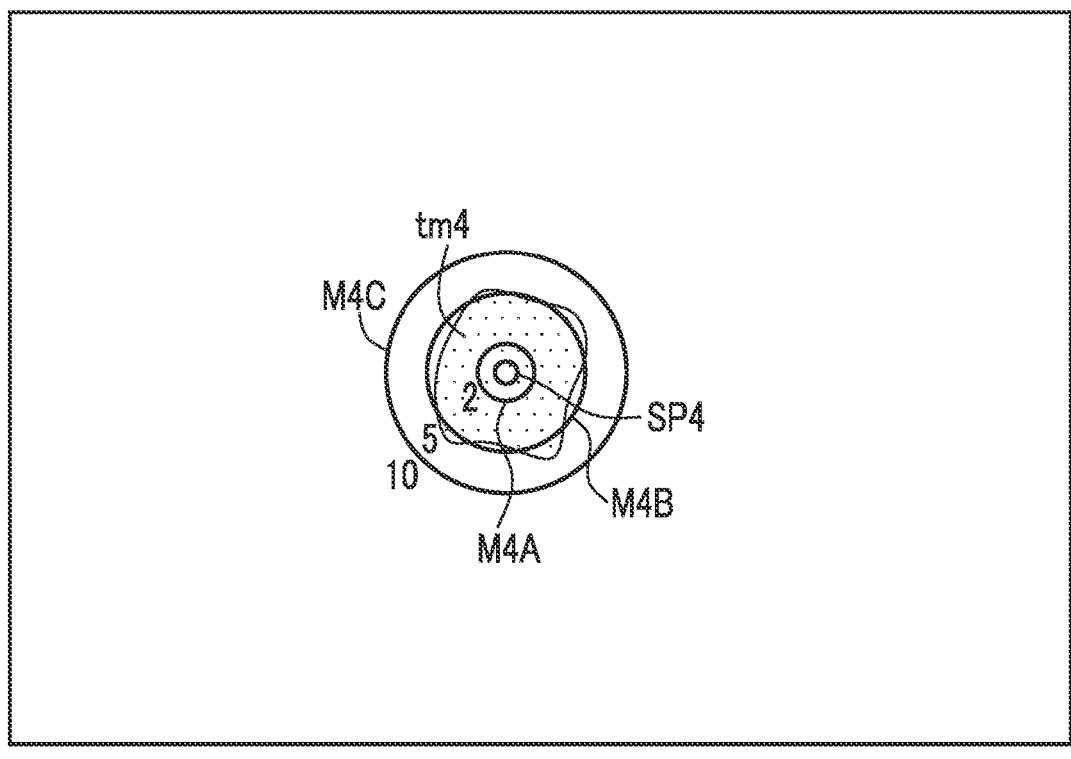
FIG. 14 is a diagram illustrating first measurement markers having a cruciform shape with gradations, a distorted cruciform shape, a circular-and-cruciform shape, and the shape of a measurement point group.
FIG. 15 is an image diagram showing three concentric circular markers having the same color.

Further, the first measurement marker corresponding to the actual size of the subject, which is 5 mm, is displayed in FIGS. 11 to 13, but the actual size of the subject may be set to any value (for example, 2 mm, 3 mm, 10 mm, or the like) according to an object to be observed or the purpose of observation. Furthermore, the first measurement marker has a cruciform shape where a vertical line and a horizontal line are orthogonal to each other in FIGS. 11 to 13, but may have a cruciform shape with gradations where gradations Mt are given to at least one of a vertical line or a horizontal line of a cruciform shape as shown in FIG. 14. Further, the first measurement marker may have a distorted cruciform shape of which at least one of a vertical line or a horizontal line is inclined. Furthermore, the first measurement marker may have a circular-and-cruciform shape where a cruciform shape and a circle are combined with each other. In addition, the first measurement marker may have the shape of a measurement point group where a plurality of measurement points EP corresponding to an actual size from a spot are combined with each other. Further, one first measurement marker may be displayed or a plurality of first measurement markers may be displayed, and the color of the first measurement marker may be changed according to an actual size.

Furthermore, as shown in FIG. 15, three concentric circular markers M4A, M4B, and M4C having different sizes (diameters as the sizes are 2 mm, 5 mm, and 10 mm, respectively) may be displayed in the first picked-up image as the first measurement marker so that a spot SP4 formed on a tumor tm4 is positioned at the centers of the markers. Since the three concentric circular markers are displayed as a plurality of markers, time and effort required to switch a marker can be saved and measurement can be performed even in a case where a subject has a non-linear shape. In a case where a plurality of concentric circular markers are to be displayed so that a spot is positioned at the centers of the concentric circular markers, a size and a color are not designated for each marker and combinations of a plurality of conditions may be prepared in advance and one can be selected from these combinations.

Figure 16:
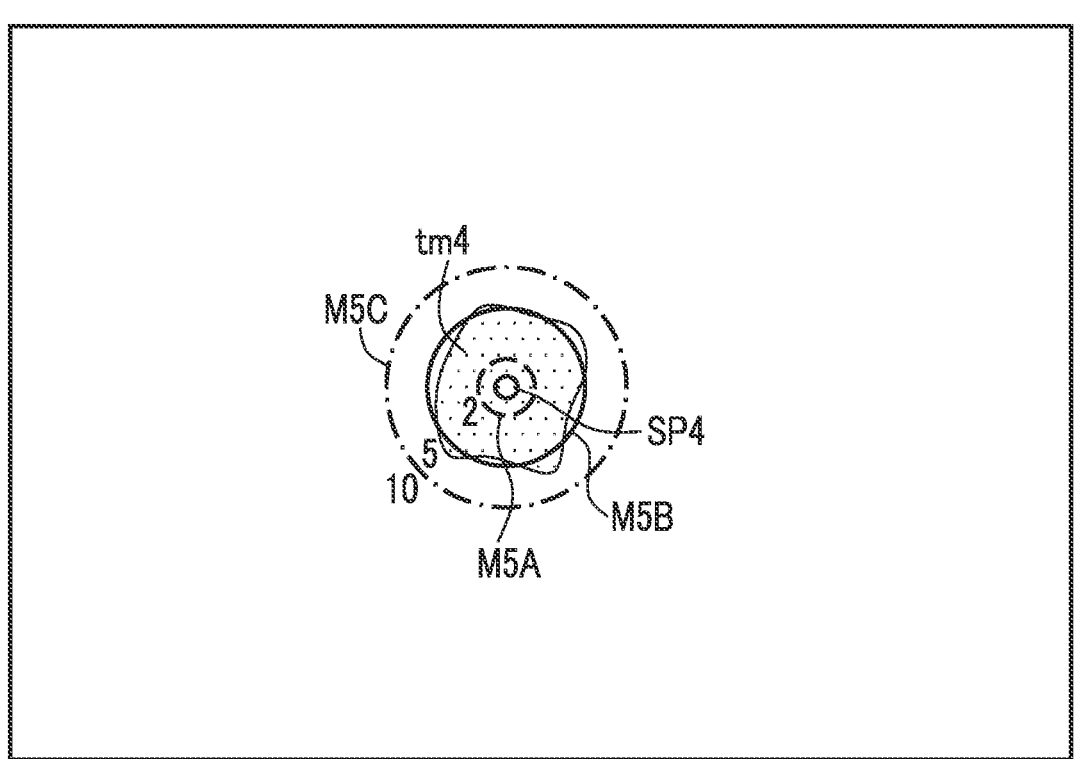
FIG. 16 is an image diagram showing three concentric circular markers having different colors.

In FIG. 15, all the three concentric circular markers are displayed with the same color (black). However, in a case where a plurality of concentric circular markers are to be displayed, a plurality of color concentric circular markers of which colors are different from each other may be used. As shown in FIG. 16, a marker M5A is displayed by a dotted line representing a red color, a marker M5B is displayed by a solid line representing a blue color, and a marker MSC is displayed by a one-dot chain line representing a white color. Since identifiability can be improved in a case where the colors of the markers are different from each other in this way, measurement can be easily performed.

Figure 17:
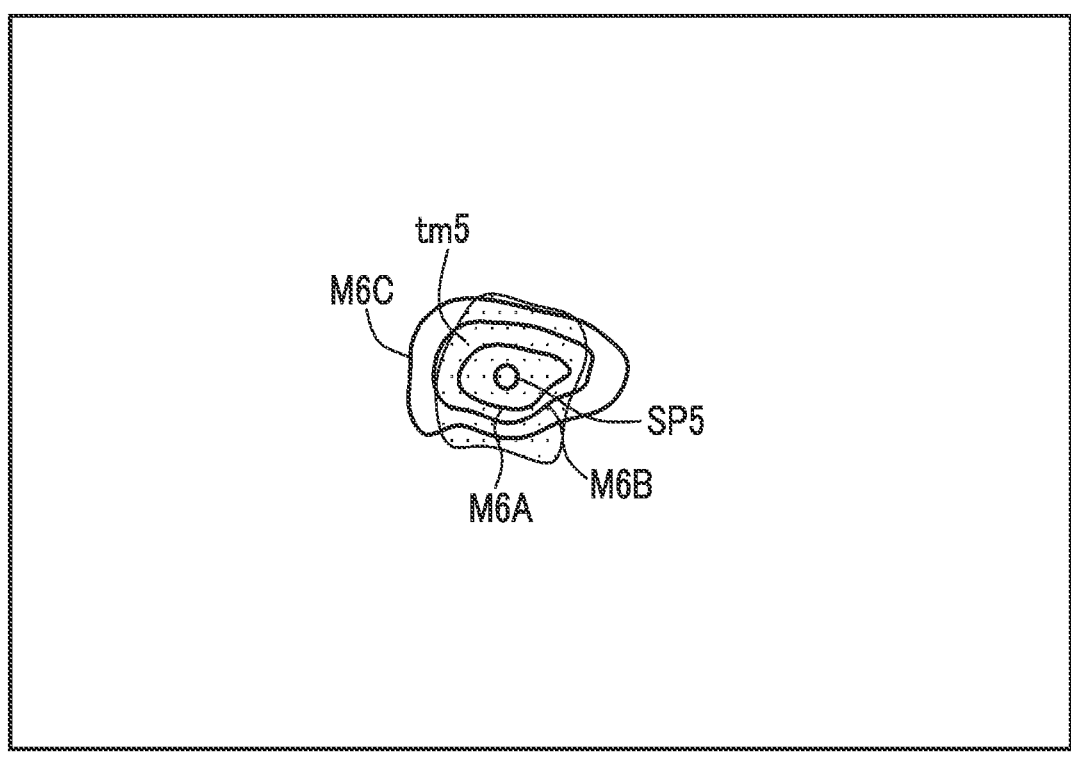
FIG. 17 is an image diagram showing distorted concentric circular markers.

Further, as shown in FIG. 17, a plurality of distorted concentric circular markers, which are distorted from the respective concentric circles, may be used as the first measurement marker other than the plurality of concentric circular markers. In this case, distorted concentric circular markers M6A, M6B, and M6C are displayed in the first picked-up image so that a spot SP5 formed on a tumor tm5 is positioned at the centers of the distorted concentric circular markers.

Figure 18:
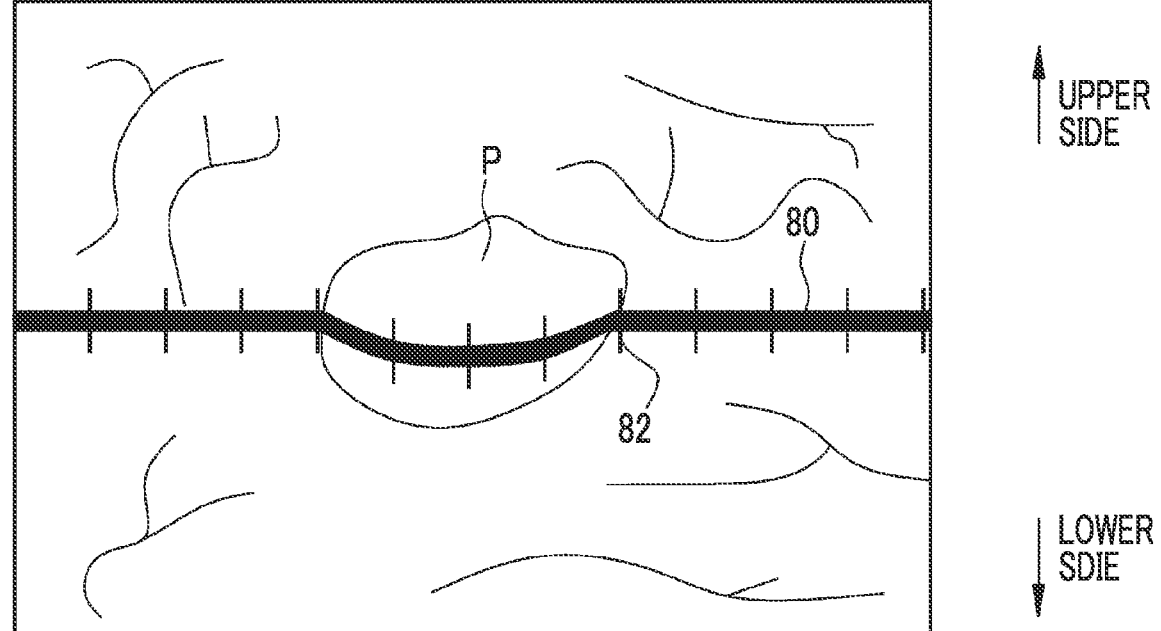
FIG. 18 is an image diagram showing a crossing line and gradations.

Light that forms a spot in a case where a subject is irradiated with the light is used as auxiliary measurement light, but other light may be used. For example, planar auxiliary measurement light that forms a crossing line 80 on a subject as shown in FIG. 18 in a case where the subject is irradiated with light may be used. In this case, a second measurement marker that consists of the crossing line 80 and gradations 82 formed on the crossing line and serving as an index of the size of the subject (for example, a polyp P) is generated as a measurement marker. In a case where planar auxiliary measurement light is used, the position specifying section 50 specifies the position of the crossing line 80 (specific region). An observation distance is shorter as the crossing line 80 is positioned closer to the lower side, and an observation distance is longer as the crossing line 80 is positioned closer to the upper side. For this reason, an interval between the gradations 82 is larger as the crossing line 80 is positioned closer to the lower side, and an interval between the gradations 82 is smaller as the crossing line 80 is positioned closer to the upper side.

In the embodiment, the hardware structures of processing units, which perform various kinds of processing, such as the signal processing unit 39, the display control unit 40, and the system control unit 41, are various processors to be described later. Various processors include: a central processing unit (CPU) that is a general-purpose processor functioning as various processing units by executing software (program); a programmable logic device (PLD) that is a processor of which the circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope apparatus
12: endoscope
12a: insertion part
12b: operation part
12c: bendable part
12d: distal end part
12e: angle knob
13a: mode changeover switch
13b: freeze switch
14: light source device
16: processor device
18: monitor (display unit)
19: user interface
20a: first hole portion
20b: second hole portion
21: objective lens
22: transparent lid (transparent member)
22a: flat surface
22b: back
23: illumination lens
24: opening
25: air/water supply nozzle
26: light source unit
27: light source control unit
28: light guide
29a: illumination optical system
29b: image pickup optical system
30: auxiliary measurement light optical system
30a: light source
30b: auxiliary measurement light-generating element
30c: prism
30d: light-emitting surface
31, 100: prism (transparent member, optical member)
31a: first close contact surface (close contact surface)
31b: second close contact surface
32: image pickup element
33: image pickup control unit
34: CDS/AGC circuit
35: A/D converter
36: communication interface (I/F)
38: communication interface (I/F)
39: signal processing unit
40: display control unit
41: system control unit
42: static image storage unit
43: static image storage control unit
45: solid line (boundary line of visual field of image pickup optical system 29b)

46: dotted line (boundary lines of central region of visual field of image pickup optical system 29*b*)
50: position specifying section
52: measurement marker setting section
54: marker table
80: crossing line
82: gradation
Ax: image pickup optical axis
Lm: auxiliary light optical axis
D1: first direction
D2: second direction
Rx: range of observation distance
Px: near end of range Rx
Py: intermediate vicinity of range Rx
Pz: far end of range Rx
Qx, Qy, Qz: image pickup range
Mt: gradation
EP: measurement point
Mx, Mx1, Mx2, Mx3: cruciform measurement marker
M4A, M4B, M4C, M5A, M5B, M5C: concentric circular marker
M6A, M6B, M6C: distorted concentric circular marker
tm, tm1, tm2, tm3, tm4, tm5: tumor
SP, SP1, SP2, SP3, SP4, SP5: spot
P: polyp
What is claimed is:
1. An endoscope comprising:
a first hole portion and a second hole portion that are provided at a distal end of an insertion part;
an image pickup optical system that is housed in the first hole portion;
an auxiliary measurement light optical system that is housed in the second hole portion and emits auxiliary measurement light, of which an optical axis is inclined with respect to an optical axis of the image pickup optical system, toward the optical axis of the image pickup optical system from a light-emitting surface thereof disposed in the second hole portion; and
a transparent member that includes a flat surface flush with the distal end of the insertion part and is inserted into an optical path of the auxiliary measurement light emitted from the light-emitting surface,
wherein the light-emitting surface is an inclined plane directed toward the optical axis of the image pickup optical system,
wherein the transparent member includes a close contact surface that is in close contact with the light-emitting surface,
a space between the close contact surface and the flat surface on the optical path of the auxiliary measurement light is made airtight by the transparent member, and
wherein an optical refractive index of a medium positioned on one side of the light-emitting surface close to the auxiliary measurement light optical system among mediums positioned on the optical path of the auxiliary measurement light is lower than an optical refractive index of a medium positioned on the other side thereof close to the transparent member.
2. The endoscope according to claim 1,
wherein the transparent member functions as a lid that closes the second hole portion.
3. The endoscope according to claim 1,
wherein the transparent member includes an optical member, and
the close contact surface is formed on the optical member.
4. The endoscope according to claim 1,
wherein the transparent member includes a transparent filling material that is filled between the close contact surface and the flat surface, and
the filling material is in close contact with the light-emitting surface, so that the close contact surface is formed.
5. The endoscope according to claim 1,
wherein the optical axis of the image pickup optical system and the optical axis of the auxiliary measurement light optical system cross each other.
6. The endoscope according to claim 5,
wherein a distance between the distal end of the insertion part and an intersection between the optical axis of the image pickup optical system and the optical axis of the auxiliary measurement light optical system is in a range of 8 mm or more and 12 mm or less.
7. The endoscope according to claim 1,
wherein the auxiliary measurement light is linear parallel light.
8. An endoscope apparatus comprising:
the endoscope according to claim 1; and
a processor configured to:
specify a position of a specific region formed by the auxiliary measurement light from a region included in a picked-up image obtained by the image pickup optical system; and
cause a display to display a specific image in which a measurement marker set according to the position of the specific region is displayed in the picked-up image.
9. The endoscope according to claim 1,
wherein the transparent member includes a flat surface through which the auxiliary measurement light is emitted.
10. The endoscope according to claim 1,
wherein the second hole portion terminates at an outermost surface of the distal end of the insertion part; and
a shape of the transparent member matches a shape of the second hole portion that terminates at the outermost surface of the distal end of the insertion part.
11. The endoscope according to claim 1,
wherein the image pickup optical system includes a plurality of lenses, and a proximal end of the transparent member is positioned closer to the proximal end of the insertion part than a proximal end of a most distal lens among the plurality of lenses.

* * * * *